United States Patent [19]

Bagner et al.

[11] 4,423,211

[45] Dec. 27, 1983

[54] PROCESS FOR THE WHOLE BROTH EXTRACTION OF AVERMECTIN

[75] Inventors: Carl Bagner, Paramus; Arthur S. Wildman, Martinsville, both of N.J.

[73] Assignee: Merck & Co., Inc., Rahway, N.J.

[21] Appl. No.: 332,418

[22] Filed: Dec. 21, 1981

[51] Int. Cl.³ .............................................. C07H 1/08
[52] U.S. Cl. .................. 536/16.9; 536/16.8; 536/7.1; 536/18.5
[58] Field of Search ...................... 536/16.8, 16.9, 7.1, 536/18.5

[56] References Cited

U.S. PATENT DOCUMENTS

| | | | |
|---|---|---|---|
| 4,160,083 | 7/1979 | Cole et al. | 536/7.1 |
| 4,160,084 | 7/1979 | Miller et al. | 536/7.1 |
| 4,160,861 | 7/1979 | Cole et al. | 536/7.1 |
| 4,161,583 | 7/1979 | Wilson et al. | 536/7.1 |
| 4,172,940 | 10/1979 | Chaiet | 536/7.1 |
| 4,199,569 | 4/1980 | Chabala et al. | 536/7.1 |
| 4,285,963 | 8/1981 | Arison et al. | 536/7.1 |
| 4,310,519 | 1/1982 | Albers-Schonberg et al. | 536/7.1 |

*Primary Examiner*—Johnnie R. Brown
*Attorney, Agent, or Firm*—David L. Rose; Mario A. Monaco; Edmunde D. Riedl

[57] ABSTRACT

A process for the whole broth extraction of avermectins wherein the pH of the whole broth is adjusted with mineral acid and then contacted with a solvent extractant so that the avermectic active component is taken up by the solvent. The now avermectin rich extractant is then processed through a solvent concentration step and the avermectin isolated by conventional crystallization. The extractant is then recycled with appropriate make-up to extract a subsequent batch of whole broth.

10 Claims, 1 Drawing Figure

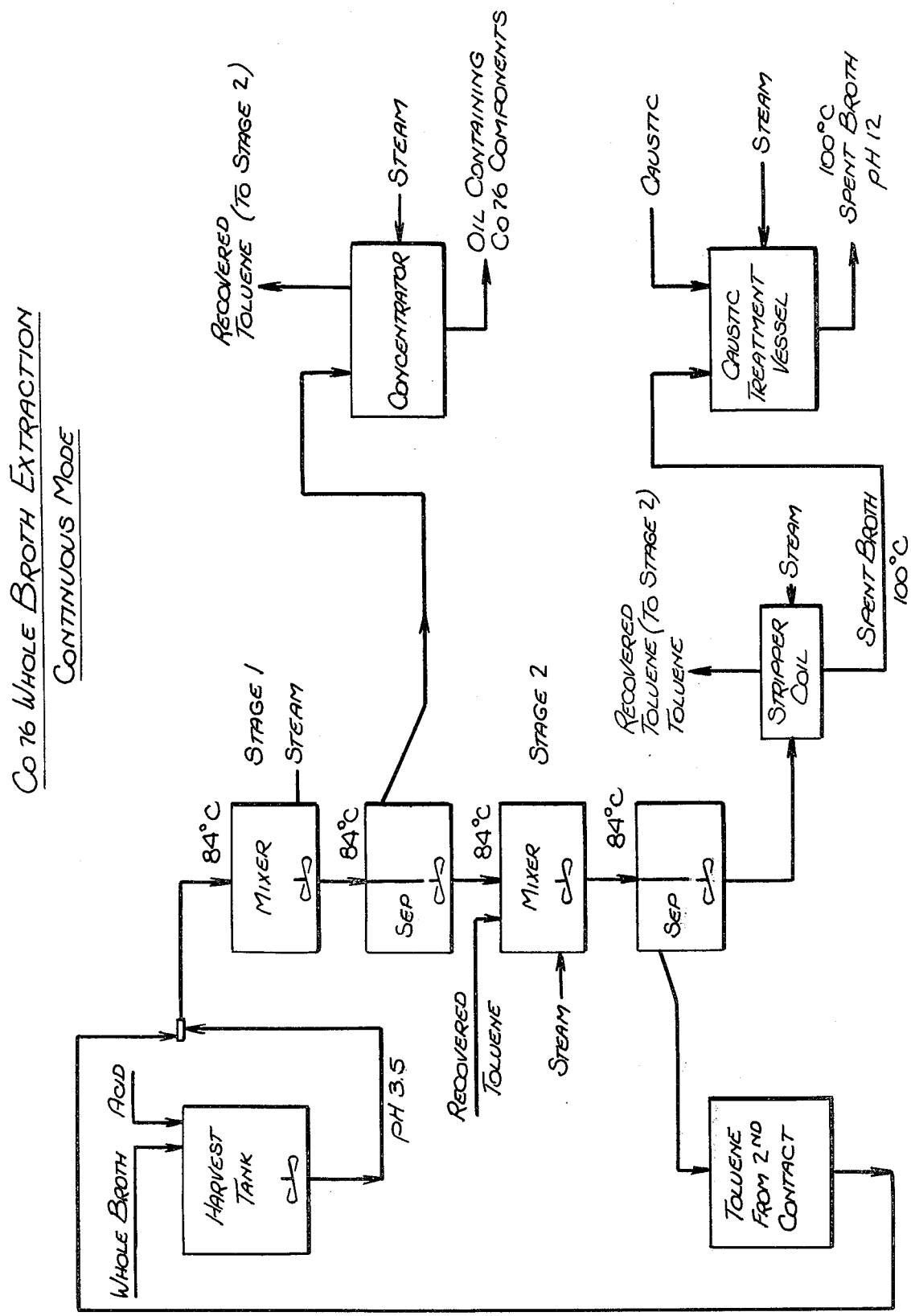

PROCESS FOR THE WHOLE BROTH EXTRACTION OF AVERMECTIN

DISCLOSURE OF THE INVENTION

This invention relates to a process for the whole broth extract of avermectins. More particularly, it relates to a process for the direct extraction of avermectin from whole broth without the use of any filter aid.

The avermectins are products produced by known fermentation methods, for example, see U.S. Pat. No. 4,199,569. In the past, the whole broth was filtered employing a filter aid material. The resulting wet filter cake was then contacted with an extracting agent usually toluene, and then the water was removed by azeotropic distilliation. The slurry comprising the extractant, the mycelia and the filter aid material was then refiltered and the extractant solution of avermectin concentrated and crystallized. The major disadvantages of this prior art process is that it requires the use of a filter aid material, which can not be disposed of until after the final separation step. This presents serious problems of waste disposal because the avermectins, when highly concentrated, are potentially toxic materials. Thus, in the past the disposal of the filter aid which contained potentially toxic residual avermectin constituted a disposal hazard that was solved only by incineration or other such drastic disposal means.

The process of this invention eliminates the need to filter the whole broth and hence the use of any filter aid material since a process is employed wherein the extraction is performed directly upon an avermectin whole broth. Furthermore, to avoid toxicity problems associated with their manufacture, not their use, the manufacturing can here be conducted in an isolated closed system and only crystallized material during the packaging step removed from the system. This process also eliminates any problems associated with the disposal of spent mycelia, and can better be understood by reference to the accompanying drawing which is a flow chart depicting the invention.

Briefly, the process of this invention entails adjusting the pH of the whole broth within the range of 1.5 to 6, more desirably within the range pH 2 to 4.2 and most preferably within the pH range 3 to 4 with mineral acid. A pH in excess of 7 is to be avoided since neutral or basic conditions decompose the avermectin. The acid employed can be any mineral acid such as sulfuric, hydrochloric, nutric, or other strong acid, although sulfuric is preferred. The whole broth is intimately contacted with and agitated with an extractant exemplified by toluene and the avermectin components dissolved into and taken up by the extractant. The solution comprising the avermectin and the extractant is then passed through a separator to strip off the extractant, and the remaining avermectin isolated by crystallization or other appropriate means known in the art. The stripped off extractant is recycled to perform its function on a subsequent batch of whole broth. The process will now be discussed in detail.

Into an appropriate vessel there is fed the whole broth from an avermectin fermentation that has been admixed with sufficient mineral acid to adjust the pH of the whole broth to between 1.5 and 2 to 6.0. After sufficient aggitation to fully adjust the pH of this whole broth, adding additional increments of acid as necessary, there is added to the pH adjusted broth sufficient extractant such that the extractant to broth ratio is from 0.2 to 1.0 or greater in volume. A ratio of 2 or 3 can be satisfactorily used, but will generally introduce more extractant than necessary. If desired, a commercially available flocculent can then be added to achieve a more efficient extraction of the whole broth.

The admixture of whole broth, extractant and optional flocculent is heated by an appropriate means, preferably a steam jacket to a temperature of from 20° C. to 100° C. or to the reflux temperature of the extractant. Unless appropriate containment and pressurization means are employed, the temperature to which the admixture is heated should not exceed the reflux temperature of the extractant employed. The sequence of addition of acid and extractant is not critical and if desired, the extranctant can be added after heating the acidified whole broth. After either continuously or intermittently agitating the heated whole broth-extractant admixture for about 1–4 hours or more it is allowed to settle. After settling, the avermectin enriched extractant fraction is then decanted and transferred to an appropriate vessel for crystallization.

While this decantation step can be performed in a single vessel, it is generally preferred to transfer the admixture to equipment more appropriate to perform a decantation. Thus, the decanted avermectin rich extractant is most preferably transfered to a concentrator where by means well known in the art the extractant is stripped from the fraction leaving an oil containing the avermectin components. The recovered extractant is then returned to the beginning of the process together with what make-up may be required to bring the extractant broth ratio to the desired level.

The nondecantable residue is treated as follows, preferably by being fed to a second mixer where it again is agitated and heated generally within the same time period and temperatures as previously described in regard to the whole broth extractant admixture.

After heating and agitating for the desired period, the spent broth and extractant are separated from the residue. Most preferably the residue is transferred from the second mixer to a separator where the extractant is decanted and recycled to the initial step. This decantation step can, if desired, be performed in the second mixer, but is preferably done in equipment especially suited to removal of the extractant fraction from the residue.

Whatever then remains from the second mixer or a subsequent separation vessel is spent broth combined with small quantities of extractant and flocculent material. These remains are then fed to a stripper where whatever remaining extractant can be recovered. This is suitably accomplished by heating the remains above the reflux temperature of the extractant. Whatever extractant that comes off is returned to the first or second mixer, and preferably the second.

Whatever residue eminates from the stripper is fed to a caustic bath heated to a temperature of from 80° to 100° C. Therein the spent broth is subjected to from ½ to 2 hours of heating at a pH 8 and preferably about a pH of 12. This exposure to heat at elevated pH decomposes the avermectins and renders the discharge of the spent broth non-hazardous.

The following is a description of the preferred mode of carrying out this invention.

A bath of avermectin whole broth containing about 40 Kg. (pure basis) of avermectin was extracted by the following procedure: The broth was adjusted to pH 2.5 with dilute $H_2SO_4$ in the harvest tank and transferred to a 20,000 gallon extractor where it was heated to 80° C. A second pH adjustment may be required. After a 2 hour heat treatment approximately 4000 (20% of broth volume) gallons of lean toluene from the previous batch was added. The batch was extracted for 3 hours. Just prior to the end of the extraction period the pH is readjusted to 5.5 with aqueous NaOH. The caustic addition was made using an eductor so that the 50% caustic used is diluted with water before reaching the batch. Six gallons of flocculating agent (Calgon WT-2640 was then added. Lesser or greater amounts of flocculating agent can be employed. The batch was then fed through a two stage continuous extraction train. Rich toluene and extracted whole broth were separated in a decanter. The rich toluene containing about 95% of the batches avermectin content was set for isolation of product. Extracted broth was then mixed with toluene in a second stage mixer. This mixture overflowed to a decanter where lean toluene and spent broth were separated. Lean toluene was then collected for use in the next batch.

Suitable extractants for use in this invention include those organic solvents that are not miscible with water to any appreciable degree and are solvents for and inert to reaction with avermectin or other components of the extraction process. These include toluene, xylene, and other aromatics including benzene, although benzene is generally to be avoided because of its suspected carcinogenicity. Other suitable solvents include the halogenated aromatics such as chlorotoluene, chlorobenzene, and the like, as well as other non-aromatic solvents such as N-butanol and other alcohols of from 4–8 carbon atoms as well as methylene chloride.

Now having described the invention, there will become evident varients which are obvious to one skilled in the art, which varients do not depart from the spirit of the following claims.

What is claimed:

1. A process for separating an avermectin rich fraction from an avermectin containing whole fermentation broth comprising acidifying the whole broth to a pH of from 1.5 to 6; admixing the acidified whole broth with an extractant in which the avermectins are soluble selected from toluene, xylene, benzene, chlorotoluene, chlorobenzene and alcohols of from 4 to 8 carbon atoms in a ratio of extractant to broth of from 0.2 to 3 in volume; heating the admixture of whole broth and extractant to a temperature of from about 20° C. to 100° C. or to the reflux temperature of the extractant in a first stage for a period of at least 1 hour; decanting the avermectin containing extractant fraction from the admixture; stripping the extractant from the avermectin containing extractant fraction; and collecting the avermectin.

2. A process according to claim 1 wherein the extractant is toluene.

3. A process according to claim 1 wherein the ratio is from 0.2 to 1.

4. A process according to claim 1 wherein the heating is accompanied by agitation.

5. A process according to claim 1 wherein the heating is conducted for a period of from 1 to 4 hours.

6. A process according to claim 1 where the pH is from about 2 to 4.2.

7. A process according to claim 1 where the stripped extractant is recycled to a first stage extract a subsequent aliquot of whole broth.

8. A process according to claim 1 where the residue from the decantation step is heated in a second stage to a temperature up to the reflux temperature of the extractant or 100° C. for a period of at least 1 hour and then decanting off the extractant fraction.

9. A process according to claim 8 where the decanted extractant is recycled to extract a subsequent aliquot portion of whole broth.

10. A process according to claim 9 where the residue is stripped of extractant, returning the extractant to said first or second stages, and the residue from the stripping is treated with caustic at a pH in excess of 7 to render the spent broth residue essentially free of active avermectin.

* * * * *